(12) United States Patent
Fronabarger et al.

(10) Patent No.: US 8,404,897 B2
(45) Date of Patent: Mar. 26, 2013

(54) FACILE SYNTHESIS OF 3-AMINOPICRIC ACID

(75) Inventors: John W. Fronabarger, Sun Lakes, AZ (US); Michael D. Williams, Gilbert, AZ (US)

(73) Assignee: Pacific Scientific Energetic Materials Company, Chandler, AZ (US)

( * ) Notice: Subject to any disclaimer, the term of this patent is extended or adjusted under 35 U.S.C. 154(b) by 110 days.

(21) Appl. No.: 12/939,012

(22) Filed: Nov. 3, 2010

(65) Prior Publication Data

US 2011/0105800 A1 May 5, 2011

Related U.S. Application Data

(60) Provisional application No. 61/257,721, filed on Nov. 3, 2009.

(51) Int. Cl.
*C07C 209/00* (2006.01)
(52) U.S. Cl. ........................................... 564/394
(58) Field of Classification Search ............... None
See application file for complete search history.

(56) References Cited

U.S. PATENT DOCUMENTS

| | | | |
|---|---|---|---|
| 3,062,885 A | 11/1962 | Kaplan | |
| 6,069,277 A | 5/2000 | Mitchell et al. | |
| 7,057,073 B2 | 6/2006 | Mitchell et al. | |
| 2009/0223401 A1 | 9/2009 | Fronabarger et al. | |

FOREIGN PATENT DOCUMENTS

| | | | | |
|---|---|---|---|---|
| DE | 243079 | * | 7/1910 | ................ 564/394 |
| WO | WO2009114347 | | 9/2009 | |

OTHER PUBLICATIONS

International Preliminary Report on Patentability dated May 18, 2012 in related Application No. PCT/US2010/055248, pp. 1-3.
International Search Report and Written Opinion dated Feb. 18, 2011 in related Application No. PCT/US2010/055248, pp. 1-3.
Borsche and Feske, "Uber den wechselseitigen Austausch von aromatisch gebundenem Hydroxyl und Halogen", *Chemische Berichte*, 61:690-702 (1928).
Katritzky, et al., "Direct Amination of Nitrogenzenes by Vicarious Nucleophilic Substitution," *Journal of Organic Chemistry*, 51(25):5039-5040 (1986).
Makosza, et al., "Vicarious Nucleophilic Substitution of Hydrogen," *Acc. Chem. Res.*, 20:282-289 (1987).
Mitchell, et al., A Versatile Synthesis of 1,3,5-Triamino-2,4,6-Trinitrobenzene (TATB), 37th International Institute of Chemical Technology (ICT) Conference, Karlsruhe, Germany (2006).
Pagoria, et al., "1,1,1-Trimethylhydrazinium Iodide: A Novel, Highly Reactive Reagent for Aromatic Amination via Vicarious Nucleophilic Substitution of Hydrogen," *J. Org. Chem.*, 61 :2934-2935 (1996).

* cited by examiner

*Primary Examiner* — Johann Richter
*Assistant Examiner* — Clinton Brooks
(74) *Attorney, Agent, or Firm* — Dean W. Russell; Tiffany L. Williams; Kilpatrick Townsend & Stockton LLP

(57) ABSTRACT

Embodiments of methods for preparing 3-aminopicric acid from picric acid is described. In one embodiment, the method comprises combining lithium hydroxide, picric acid, and a first solvent to form a first solution, combining lithium hydroxide, hydroxylamine hydrochloride, and a second solvent to form a second solution, combining the first solution with the second solution to form a mixture, and cooling the mixture.

18 Claims, 3 Drawing Sheets

FACILE SYNTHESIS OF 3-AMINOPICRIC ACID

CROSS REFERENCE TO RELATED APPLICATIONS

This application is related to and claims priority benefits from U.S. Provisional Application Ser. No. 61/257,721, filed on Nov. 3, 2009, entitled FACILE SYNTHESIS OF 3-AMINOPICRIC ACID. The '721 application is hereby incorporated in its entirety by this reference.

FIELD OF THE INVENTION

This invention relates to explosives, and in particular to preparation of a potential intermediate in the synthesis of a lead-free primary explosive.

BACKGROUND

Primary explosives are sensitive explosive materials that are used, in relatively small quantities, to initiate a secondary or main explosive charge. Primary explosives are commonly used in percussion primers and electric primers (hot-wire igniters) to initiate an explosion. Conventionally, these primer compositions were based on lead-containing components, such as lead styphnate. The use of lead-containing material is undesirable from an environmental standpoint since its use and manufacture can contribute to or cause lead contamination.

In response, a "green" alternative to lead-containing primer compositions was developed, in which the lead styphnate or similar material is replaced with a lead-free material, One such example of a lead-free replacement for lead styphnate is 4,6-dinitro-7-hydroxybenzofuroxan, potassium salt ("KDNP"), the details of which are described in U.S. Publication No. 2009/0223401.

During the development of KDNP for replacement of lead styphnate, it became apparent that 3-aminopicric acid, also known as 3-ANP or 3-amino-2,4,6-trinitrophenol, would be a suitable synthetic intermediate. Prior art teaches that 3-ANP may be formed by reaction of water on 2,3,4,6-tetranitroaniline. However, 2,3,4,6-tetranitroaniline is difficult to prepare and exists as an unstable explosive material.

An alternative starting material to 2,3,4,6-tetranitroaniline is picric acid. Picric acid is a desirable starting material to form 3-ANP because commercial picric acid is readily available and is typically less expensive than 2,3,4,6-tetranitroaniline. Moreover, a possible source of picric acid includes Explosive D (also known as Dunnite or ammonium picrate). Explosive D is stockpiled in large quantities for military purposes and some amount of this material may be scheduled for decommissioning. To avoid decommissioning costs, Explosive D could potentially be converted to picric acid and subsequently to 3-ANP. Use of Explosive D as a source of picric acid would avoid any initial nitration process and resulting waste disposal costs to afford a truly "green" synthetic methodology.

Conversion of picric acid to 3-ANP requires a reaction process to substitute an amino group in place of a hydrogen. A reaction methodology known as vicarious nucleophilic substitution ("VNS") is commonly used in energetics chemistry to replace a hydrogen with an amino group on an electrophilic (highly nitrated) aromatic ring, particularly in the preparation of DATB, TATB, and related materials. See M. Makosza and J. Winiarski, Acc. Chem. Res. 1987, 20, 282; U.S. Pat. No. 6,069,277. The general experimental protocol for VNS involves reacting nitroarenes or sufficiently activated aromatics with hydroxylamine in either aqueous or organic solvent and often in the presence of a base such as KOH, NaOH or t-BuOK. See A. R. Katritzky and K. S. Laurenzo, J. Org. Chem., 1986, 51 (25), 5039-5040. 1,1,1-Trimethylhydrazinium iodide has also been proven to be a highly reactive reagent for aminations of nitro-aromatic compounds. See P. F. Pagoria, A. R. Mitchell, R. D. Schmidt, J. Org. Chem., 1996, 61, 2934-2935.

Converting picric acid (either commercial picric acid or picric acid derived from Explosive D) to 3-ANP in an aqueous system via the standard VNS experimental protocol is problematic. The aqueous solvents did not perform well because of the highly insoluble nature of the sodium or potassium picrate salts. Potassium picrate is extremely insoluble in water, the sodium analog is only very slightly soluble, and the solubilities of both compounds are not improved by addition of methanol. As a result, aminations of picric acid utilizing hydroxylamine/base give extremely low yields of 3-ANP and are unsuitable from a synthetic standpoint.

Due to the desire to have an inexpensive and green process for producing 3-ANP from picric acid, it is desirable to find a method to produce 3-ANP from picric acid in an aqueous system, particularly in situations where large amounts of solvent or large scale reactions are required.

SUMMARY

Embodiments of the present invention comprise methods of preparing 3-aminopicric acid from picric acid. In one embodiment, the method comprises combining lithium hydroxide, picric acid, and a first solvent to form a first solution, combining lithium hydroxide, hydroxylamine hydrochloride, and a second solvent to form a second solution, combining the first solution with the second solution to form a mixture, and cooling the mixture. In some embodiments, the first solvent and the second solvent are water.

In some embodiments, the second solution is formed by combining the lithium hydroxide and the second solvent to form a lithium hydroxide solution, combining the hydroxylamine hydrochloride and the second solvent to form a hydroxylamine hydrochloride solution, and adding the hydroxylamine hydrochloride solution to the lithium hydroxide solution.

In some embodiments, a precipitate is formed in the mixture. The precipitate may be separated from the mixture and an acid may be added to an aqueous suspension of the precipitate to obtain a product.

DETAILED DESCRIPTION

Figure 1:
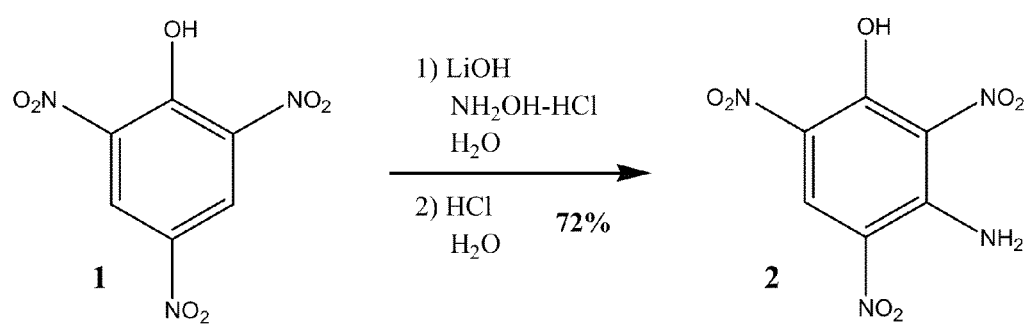
FIG. 1 is a depiction of the synthetic method used for preparation of 3-ANP.

Embodiments of the invention include methods for preparing 3-aminopicric acid from picric acid. In one embodiment, such as the example depicted in FIG. 1, 3-aminopicric acid is prepared by reacting picric acid, hydroxylamine hydrochloride, and lithium hydroxide in a suitable solvent.

In some embodiments, hydroxylamine hydrochloride may be supplied in a molar ratio of about 2 moles to about 5 moles per mole of picric acid, and lithium hydroxide may be supplied in a molar ratio of about 2.5 moles to about 20 moles per mole of picric acid. For example, in one embodiment, hydroxylamine hydrochloride may be supplied in a molar ratio of about 2 moles per mole of picric acid, while 12.5 moles of lithium hydroxide may be supplied per mole of picric acid.

The solvent may be supplied in an amount that is suitable to effectuate the reaction between picric acid, hydroxylamine hydrochloride, and lithium hydroxide. In some embodiments, the solvent is water or other aqueous solvents. In other alternative embodiments, the solvent includes but is not limited to tetrahydrofuran ("THF"), dimethyl sulfoxide ("DMSO"), or other polar organic solvents. In yet other embodiments, a combination of solvents may be used.

The reaction components may be combined in any order or sequence suitable to effectuate the reaction. In some embodiments, the reaction of picric acid, lithium hydroxide, and hydroxylamine hydrochloride may be carried out as follows. A first amount of lithium hydroxide, the picric acid, and a first solvent are combined to form a first solution (solution A). The concentration of lithium hydroxide in the solution A may range from about 0.01 g/mL to about 0.1 g/mL, alternatively about 0.02 g/mL. The concentration of picric acid in the solution A may range from about 0.01 g/mL to about 0.1 g/mL, alternatively about 0.07 g/mL. In some embodiments, the first solvent is water or other aqueous solvents. In other alternative embodiments, the first solvent includes but is not limited to THF, DMSO, or other polar organic solvents.

Next, a second amount of lithium hydroxide is combined with a first amount of a second solvent to form a second solution (solution B). The concentration of lithium hydroxide in the solution B may range from about 0.1 g/mL to about 0.5 g/mL, alternatively about 0.4 g/mL. In some embodiments, the second solvent is water or other aqueous solvents. In other alternative embodiments, the second solvent includes but is not limited to THF, DMSO, or other polar organic solvents. The first solvent and the second solvent may have the same composition. Alternatively, the first solvent may be water or other aqueous solvents, while the second solvent is an organic solvent, or vice versa.

The hydroxylamine hydrochloride is combined with a second amount of the second solvent to form a third solution (solution C). The concentration of hydroxylamine hydrochloride in the solution C may range from about 0.1 g/mL to about 0.5 g/mL, alternatively about 0.2 g/mL. Alternatively, the hydroxylamine hydrochloride may be combined with a third solvent, where the third solvent is water or other aqueous solvents. In other alternative embodiments, the third solvent includes but is not limited to THF, DMSO, or other polar organic solvents. The third solvent may have the same or different composition as either the first solvent or the second solvent or both.

The components may be reacted under conditions suitable to synthesize 3-aminopicric acid. For example, in some embodiments, the solution B is cooled in the temperature range of no greater than 20° C. while the solution C is added. The combined solutions B and C are then cooled in the temperature range of less than 1° C. The solution A is then added while maintaining the temperature of the resulting mixture in the range of no greater than 5° C. In other embodiments, the components may be reacted by mixing them together and then cooling the resulting mixture.

Once the resulting mixture is formed, it may be cooled in the temperature range of about −8° C. to about 25° C., alternatively in the temperature range of about −2° C. to about 5° C., alternatively to about 0° C. The duration of the cooling step may be a duration that is greater than about 1 hour, alternatively greater than about 10 hours, alternatively, about 6 hours.

The mixture is then filtered to collect a precipitate. The precipitate is washed with cold water and transferred to an aqueous suspension where an acid is added. Suitable acids include but are not limited to hydrochloric acid, sulfuric acid, or nitric acid. In one embodiment, hydrochloric acid is provided in a concentration of about 5M. The precipitate/HCL mixture is stirred at ambient temperature for about 5 minutes to 15 minutes, then filtered again to collect the precipitate. Finally, the precipitate is washed with cold water and air dried.

In this embodiment, as shown in FIG. 1, picric acid is very soluble in aqueous solution as the lithium salt, where the lithium salt underwent facile reaction with hydroxylamine hydrochloride at low temperature to afford 3-ANP in good yield. For example, in some embodiments, the method produces a reaction product with at least a 50% yield, alternatively at least 60% yield, alternatively at least 70% yield.

The products contemplated and made by the methods of the present application (in at least some aspects of the present invention, 3-ANP) may be found suitable as an intermediate product in the formulation of lead-free compounds (such as KDNP) suitable for use as replacements for lead styphnate in explosives.

EXAMPLES

The following examples demonstrate the preparation and characterization of a material as taught herein.

Example 1

Figure 2:
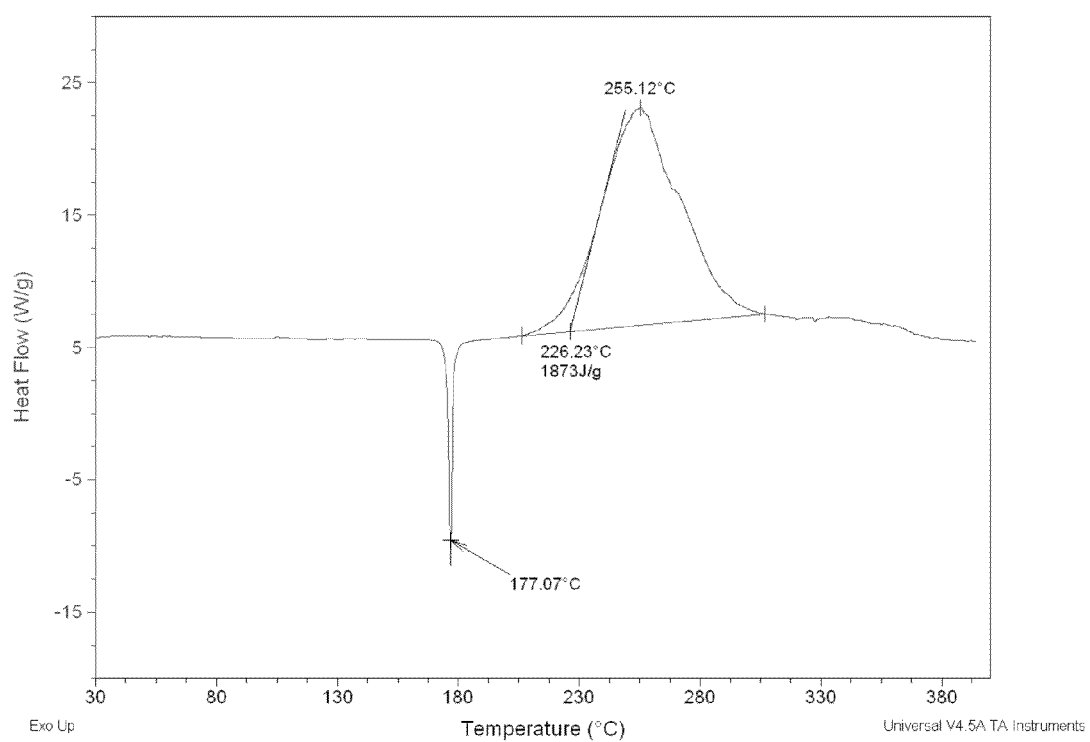
FIG. 2 shows the results of a differential scanning calorimetry (DSC) analysis on a material prepared according to the present techniques.
Figure 3:
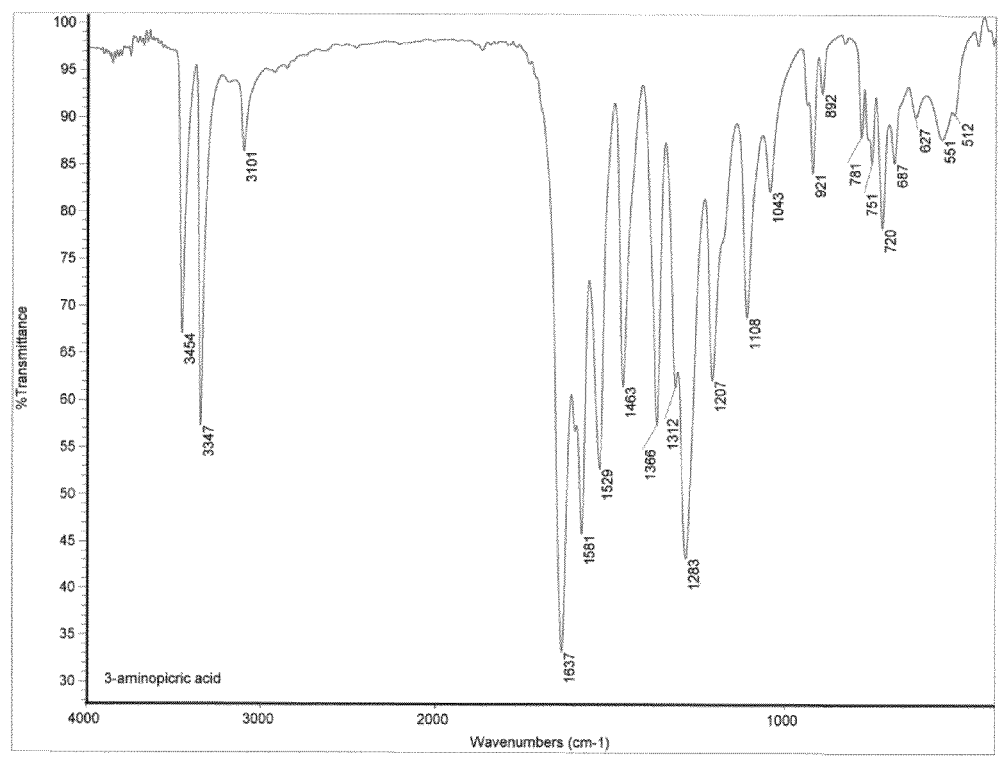
FIG. 3 shows the results of a Fourier transform infrared spectroscopic analysis on a material prepared according to the present techniques.

As an example, picric acid (38.1 g, 0.166 mol) was dissolved in 560 mL of water at room temperature by addition of 9.9 g of lithium hydroxide to give a yellow solution (solution A). Two additional solutions were prepared, a solution of 77.6 g of LiOH in 200 mL of water (solution B) and 23.90 g of hydroxylamine hydrochloride monohydrate in 120 mL of water (solution C). Solution B was cooled in a salt/ice bath and maintained at ≦20° C. while solution C was added over 5 minutes. The resulting colorless mixture was allowed to cool to <1° C. and a pre-chilled (in an ice bath) solution A was added in approximately 50 mL portions over 20 minutes with the temperature maintained ≦5° C. during the addition. The mixture was dark brown by the end of the addition and was free of solids. The mixture was stirred in the salt/ice bath for 3.5 hours (temperature range 1.5° C. to −1.1° C.) at which time a yellow precipitate (3-ANP, lithium salt) started to form. The mixture was stirred cold an additional 2.5 hours (6 hours total reaction time) and the thick bright yellow suspension was filtered over a medium frit. The yellow precipitate was washed once with cold water and then transferred into a 2 L beaker with 250 mL of water. The suspension was stirred at ambient temperature while 130 mL of 5M hydrochloric acid was added. The suspension became markedly brighter yellow on addition of HCl and was stirred for 10 minutes. The resulting 3-ANP (29.18 g) was filtered over a medium frit, washed three times with cold water and transferred to a crystallizing dish to air dry. Yield of the resulting 3-ANP product was 29.18 g (0.120 mol, 72%) as confirmed by differential scanning calorimetry (FIG. 2) and FT-Infrared spectroscopic analysis (FIG. 3).

The foregoing is provided for purposes of illustrating, explaining, and describing embodiments of the present invention. Further modifications and adaptations to these embodiments will be apparent to those skilled in the art and may be made without departing from the scope or spirit of the invention.

That which is claimed is:

1. A method for preparing 3-aminopicric acid, comprising the steps of:
   (a) combining lithium hydroxide, picric acid, and a first solvent to form a first solution;
   (b) combining lithium hydroxide, hydroxylamine hydrochloride, and a second solvent to form a second solution;
   (c) combining the first solution with the second solution to form a mixture; and
   (d) cooling the mixture.

2. The method of claim 1, wherein a molar ratio of hydroxylamine hydrochloride is about 2 moles to about 5 moles per mole of picric acid.

3. The method of claim 1, wherein a molar ratio of lithium hydroxide is about 2.5 moles to about 20 moles per mole of picric acid.

4. The method of claim 1, wherein the mixture is cooled in a temperature range of about −8 degrees C. to about 25 degrees C.

5. The method of claim 4, wherein the mixture is maintained in the temperature range for about 1 hour to about 10 hours.

6. The method of claim 1, wherein the first solvent and the second solvent are water.

7. The method of claim 1, wherein the step of combining lithium hydroxide, hydroxylamine hydrochloride, and a second solvent to form a second solution comprises:
   (a) combining the lithium hydroxide and a first amount of the second solvent to form a lithium hydroxide solution;
   (b) combining the hydroxylamine hydrochloride and a second amount of the second solvent to form a hydroxylamine hydrochloride solution; and
   (c) adding the hydroxylamine hydrochloride solution to the lithium hydroxide solution to form the second solution.

8. The method of claim 7, further comprising cooling the second solution.

9. The method of claim 8, wherein the second solution is cooled in a temperature range of less than 1 degree C.

10. A method for preparing 3-aminopicric acid, comprising the steps of:
    (a) combining lithium hydroxide, picric acid, and a first solvent to form a first solution;
    (b) combining lithium hydroxide, hydroxylamine hydrochloride, and a second solvent to form a second solution;
    (c) combining the first solution with the second solution to form a mixture;
    (d) cooling the mixture; and
    (e) forming a precipitate in the mixture.

11. The method of claim 10, further comprising the step of separating the precipitate from the mixture.

12. The method of claim 11, further comprising the step of adding hydrochloric acid to an aqueous suspension of the precipitate to obtain a product.

13. The method of claim 10, wherein a molar ratio of hydroxylamine hydroxide is about 2 moles to about 5 moles per mole of picric acid.

14. The method of claim 10, wherein a molar ratio of lithium hydroxide is about 2.5 moles to about 20 moles per mole of picric acid.

15. The method of claim 10, wherein the first solvent and the second solvent are water.

16. A method for preparing 3-aminopicric acid, comprising the steps of:
    (a) cooling an aqueous solution of lithium hydroxide;
    (b) adding an aqueous solution of hydroxylamine hydrochloride to the aqueous solution of lithium hydroxide to form a combined solution;
    (c) cooling the combined solution;
    (d) adding an aqueous solution of lithium hydroxide and picric acid to the combined solution to form a mixture;
    (e) cooling the mixture;
    (f) forming a precipitate in the mixture;
    (g) separating the precipitate from the mixture; and
    (h) adding an acid to an aqueous suspension of the precipitate to obtain a product.

17. The method of claim 16, wherein a molar ratio of hydroxylamine hydrochloride is about 2 moles to about 5 moles per mole of picric acid.

18. The method of claim 16, wherein a molar ratio of lithium hydroxide is about 2.5 moles to about 20 moles per mole of picric acid.

* * * * *